United States Patent
Ritzén et al.

(10) Patent No.: US 8,841,297 B2
(45) Date of Patent: Sep. 23, 2014

(54) PHENYLIMIDAZOLE DERIVATIVE AS PDE10A ENZYME INHIBITOR

(75) Inventors: Andreas Ritzén, Vanløse (DK); Jan Kehler, Lyngby (DK); Morten Langgård, Glostrup (DK); Jacob Nielsen, København V. (DK); John Paul Kilburn, Haslev (DK); Mohammed M. Farah, Leeds (GB)

(73) Assignee: H. Lundbeck A/S, Valby (DK)

( * ) Notice: Subject to any disclaimer, the term of this patent is extended or adjusted under 35 U.S.C. 154(b) by 68 days.

(21) Appl. No.: 13/378,405

(22) PCT Filed: Jun. 17, 2010

(86) PCT No.: PCT/DK2010/050147
§ 371 (c)(1),
(2), (4) Date: Apr. 10, 2012

(87) PCT Pub. No.: WO2010/145668
PCT Pub. Date: Dec. 23, 2010

(65) Prior Publication Data
US 2012/0190685 A1    Jul. 26, 2012

(30) Foreign Application Priority Data
Jun. 19, 2009    (WO) ................ PCT/DK2009/050134

(51) Int. Cl.
| | |
|---|---|
| *A01N 43/58* | (2006.01) |
| *A01N 43/60* | (2006.01) |
| *A61K 31/50* | (2006.01) |
| *A61K 31/495* | (2006.01) |

(52) U.S. Cl.
USPC .......................................... 514/248; 514/249

(58) Field of Classification Search
USPC ........................................................ 514/248
See application file for complete search history.

(56) References Cited

U.S. PATENT DOCUMENTS

| | | | |
|---|---|---|---|
| 4,036,840 | A | 7/1977 | O'Brien et al. |
| 7,897,619 | B2 | 3/2011 | Zeng et al. |
| 8,133,897 | B2 | 3/2012 | Ritzen et al. |
| 2008/0090891 | A1 | 4/2008 | Zelle et al. |

FOREIGN PATENT DOCUMENTS

| | | |
|---|---|---|
| TW | 200736246 A | 10/2007 |
| WO | 2004/005290 A1 | 1/2004 |
| WO | 2005/003129 A1 | 1/2005 |
| WO | 2005/082883 A2 | 9/2005 |
| WO | 2006/070284 A1 | 7/2006 |
| WO | 2007/077490 A2 | 7/2007 |
| WO | 2007/098169 A1 | 8/2007 |
| WO | 2008/001182 A1 | 1/2008 |
| WO | 2009/023179 A2 | 2/2009 |
| WO | 2010/145668 | 12/2010 |

OTHER PUBLICATIONS

U.S. Appl. No. 13/365,504, filed Feb. 3, 2012, Ritzen et al.
Kehler, J., et al., "The potential therapeutic use of phosphodiesterase 10 inhibitors", Expert Opinion in Ther. Patents, 17(2), p. 147-157, 2007.
CAS Registry No. 348125-42-8; Jul. 25, 2001.
CAS Registry No. 939690-18.3; Jun. 27, 2007.
CAS Registry No. 938887-78-6; Jun. 25, 2007.
CAS Registry No. 530154-74-6; Jun. 13, 2003.
CAS Registry No. 442570-89-0; Aug. 5, 2002.
CAS Registry No. 296791-07-6; Oct. 18, 2000.
International Search Report and Written Opinion for PCT International Application No. PCT/DK2009/050134, Oct. 8, 2010.
Taiwanese Search Report issued in TW Application No. 98119876 filed Jun. 15, 2009.
International Search Report and Written Opinion issued Jul. 27, 2010 in International Application No. PCT/DK2010/050147 filed Jun. 17, 2010.
Mark A. Geyer et al., 2002, "Animal Models Relevant to Schizophrenia Disorders", Neuropsychopharmacology: The Fifth Generation of Progress, pp. 689-701.

*Primary Examiner* — Layla Soroush
(74) *Attorney, Agent, or Firm* — Mary Catherine Di Nunzio

(57) ABSTRACT

This invention provides the compound 5,8-Dimethyl-2-[2-(1-methyl-4-phenyl-1H-imidazol-2-yl)-ethyl]-[1,2,4]thazolo[1,5-a]pyrazine and pharmaceutically acceptable acid addition salts thereof.

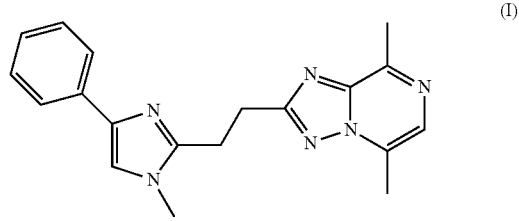

(I)

12 Claims, No Drawings

PHENYLIMIDAZOLE DERIVATIVE AS PDE10A ENZYME INHIBITOR

CROSS-REFERENCE TO RELATED APPLICATIONS

The present application is a §371 U.S. National Stage Application of International Application No. PCT/DK2010/050147, filed Jun. 17, 2010, which claims priority of International Application No. PCT/DK2009/050134, filed Jun. 19, 2009. Each of these applications is hereby incorporated by reference in its entirety.

FIELD OF THE INVENTION

The invention provides a compound that is a PDE10A enzyme inhibitor, and as such is useful to treat neurodegenerative and psychiatric disorders. The invention also provides pharmaceutical compositions comprising the compound of the invention and methods of treating disorders using the compound of the invention.

BACKGROUND OF THE INVENTION

Throughout this application, various publications are referenced in full. The disclosures of these publications are hereby incorporated by reference into this application to describe more fully the state of the art to which this invention pertains.

The cyclic nucleotides cyclic-adenosine monophosphate (cAMP) and cyclic-guanosine monophosphate (cGMP) function as intracellular second messengers regulating a vast array of processes in neurons. Intracellular cAMP and cGMP are generated by adenyl and guanyl cyclases, and are degraded by cyclic nucleotide phosphodiesterases (PDEs). Intracellular levels of cAMP and cGMP are controlled by intracellular signaling, and stimulation/repression of adenyl and guanyl cyclases in response to GPCR activation is a well characterized way of controlling cyclic nucleotide concentrations (Antoni, F. A. *Front. Neuroendocrinol.* 2000, 21, 103-132). cAMP and cGMP levels in turn control activity of cAMP- and cGMP-dependent kinases as well as other proteins with cyclic nucleotide response elements, which through subsequent phosphorylation of proteins and other processes regulate key neuronal functions such as synaptic transmission, neuronal differentiation and survival.

There are 21 phosphodiesterase genes that can be divided into 11 gene families. PDEs are a class of intracellular enzymes that regulate levels of cAMP and cGMP via hydrolysis of the cyclic nucleotides into their respective nucleotide monophosphates. Some PDEs degrade cAMP, some cGMP and some both. Most PDEs have a widespread expression and have roles in many tissues, while some are more tissue-specific.

Phosphodieasterase 10A (PDE10A) is a dual-specificity phosphodiesterase that can convert both cAMP to AMP and cGMP to GMP (Loughney, K. et al. *Gene* 1999, 234, 109-117; Fujishige, K. et al. *Eur. J. Biochem.* 1999, 266, 1118-1127 and Soderling, S. et al. *Proc. Natl. Acad. Sci.* 1999, 96, 7071-7076). PDE10A is primarily expressed in the neurons in the striatum, *n. accumbens* and in the olfactory tubercle (Kotera, J. et al. *Biochem. Biophys. Res. Comm.* 1999, 261, 551-557 and Seeger, T. F. et al. *Brain Research,* 2003, 985, 113-126).

Mouse PDE10A is the first identified member of the PDE10 family of phosphodiesterases (Fujishige, K. et al. *J. Biol. Chem.* 1999, 274, 18438-18445 and Loughney, K. et al. *Gene* 1999, 234, 109-117) and N-terminal splice variants of both the rat and human genes have been identified (Kotera, J. et al. *Biochem. Biophys. Res. Comm.* 1999, 261, 551-557 and Fujishige, K. et al. *Eur. J. Biochem.* 1999, 266, 1118-1127). There is a high degree of homology across species. PDE10A is uniquely localized in mammals relative to other PDE families. mRNA for PDE10 is highly expressed in testis and brain (Fujishige, K. et al. *Eur J Biochem.* 1999, 266, 1118-1127; Soderling, S. et al. *Proc. Natl. Acad. Sci.* 1999, 96, 7071-7076 and Loughney, K. et al. *Gene* 1999, 234, 109-117). These studies indicate that within the brain, PDE10 expression is highest in the striatum (caudate and putamen), *n. accumbens* and olfactory tubercle. More recently, an analysis has been made of the expression pattern in rodent brain of PDE10A mRNA (Seeger, T. F. et al. *Abst. Soc. Neurosci.* 2000, 26, 345.10) and PDE10A protein (Menniti, F. S. et al. William Harvey Research Conference 'Phosphodiesterase in Health and Disease', Porto, Portugal, Dec. 5-7, 2001).

PDE10A is expressed at high levels by the medium spiny neurons (MSN) of the caudate nucleus, the accumbens nucleus and the corresponding neurons of the olfactory tubercle. These constitute the core of the basal ganglia system. The MSN has a key role in the cortical-basal ganglia-thalamocortical loop, integrating convergent cortical/thalamic input, and sending this integrated information back to the cortex. MSN express two functional classes of neurons: the $D_1$ class expressing $D_1$ dopamine receptors and the $D_2$ class expressing $D_2$ dopamine receptors. The $D_1$ class of neurons is part of the 'direct' striatal output pathway, which broadly functions to facilitate behavioral responses. The $D_2$ class of neurons is part of the 'indirect' striatal output pathway, which functions to suppress behavioral responses that compete with those being facilitated by the 'direct' pathway. These competing pathways act like the brake and accelerator in a car. In the simplest view, the poverty of movement in Parkinson's disease results from over-activity of the 'indirect' pathway, whereas excess movement in disorders such as Huntington's disease represent over-activity of the direct pathway. PDE10A regulation of cAMP and/or cGMP signaling in the dendritic compartment of these neurons may be involved in filtering the cortico/thalamic input into the MSN. Furthermore, PDE10A may be involved in the regulation of GABA release in the *substantia nigra* and *globus pallidus* (Seeger, T. F. et al. *Brain Research,* 2003, 985, 113-126).

Dopamine $D_2$ receptor antagonism is well established in the treatment of schizophrenia. Since the 1950's, dopamine $D_2$ receptor antagonism has been the mainstay in psychosis treatment and all effective antipsychotic drugs antagonise $D_2$ receptors. The effects of $D_2$ are likely to be mediated primarily through neurons in the striatum, *n. accumbens* and olfactory tubercle, since these areas receive the densest dopaminergic projections and have the strongest expression of $D_2$ receptors (Konradi, C. and Heckers, S. *Society of Biological Psychiatry,* 2001, 50, 729-742). Dopamine $D_2$ receptor agonism leads to decrease in cAMP levels in the cells where it is expressed through adenylate cyclase inhibition, and this is a component of $D_2$ signalling (Stoof, J. C.; Kebabian J. W. *Nature* 1981, 294, 366-368 and Neve, K. A. et al. *Journal of Receptors and Signal Transduction* 2004, 24, 165-205). Conversely, $D_2$ receptor antagonism effectively increases cAMP levels, and this effect could be mimicked by inhibition of cAMP degrading phosphodiesterases.

Most of the 21 phosphodiesterase genes are widely expressed; therefore inhibition is likely to have side effects. Because PDE10A, in this context, has the desired expression profile with high and relatively specific expression in neurons in striatum, *n. accumbens* and olfactory tubercle, PDE10A inhibition is likely to have effects similar to $D_2$ receptor antagonism and therefore have antipsychotic effects.

While PDE10A inhibition is expected to mimic $D_2$ receptor antagonism in part, it might be expected to have a different profile. The $D_2$ receptor has signalling components besides cAMP (Neve, K. A. et al. *Journal of Receptors and Signal Transduction* 2004, 24, 165-205), for which reason interference with cAMP through PDE10A inhibition may negatively modulate rather than directly antagonise dopamine signaling through $D_2$ receptors. This may reduce the risk of the extrapyrimidal side effects that are seen with strong $D_2$ antagonism. Conversely, PDE10A inhibition may have some effects not seen with $D_2$ receptor antagonism. PDE10A is also expressed in $D_1$ receptors expressing striatal neurons (Seeger, T. F. et al. *Brain Research*, 2003, 985, 113-126). Since $D_1$ receptor agonism leads to stimulation of adenylate cyclase and resulting increase in cAMP levels, PDE10A inhibition is likely to also have effects that mimic $D_1$ receptor agonism. Finally, PDE10A inhibition will not only increase cAMP in cells, but might also be expected to increase cGMP levels, since PDE10A is a dual specificity phosphodiesterase. cGMP activates a number of target protein in cells like cAMP and also interacts with the cAMP signalling pathways. In conclusion, PDE10A inhibition is likely to mimic $D_2$ receptor antagonism in part and therefore has antipsychotic effect, but the profile might differ from that observed with classical $D_2$ receptor antagonists.

The PDE10A inhibitor papaverine is shown to be active in several antipsychotic models. Papaverine potentiated the cataleptic effect of the $D_2$ receptor antagonist haloperidol in rats, but did not cause catalepsy on its own (WO 03/093499). Papaverine reduced hyperactivity in rats induced by PCP, while reduction of amphetamine induced hyperactivity was insignificant (WO 03/093499). These models suggest that PDE10A inhibition has the classic antipsychotic potential that would be expected from theoretical considerations. WO 03/093499 further discloses the use of selective PDE10 inhibitors for the treatment of associated neurologic and psychiatric disorders. Furthermore, PDE10A inhibition reverses subchronic PCP-induced deficits in attentional set-shifting in rats (Rodefer et al. *Eur. J. Neurosci.* 2005, 4, 1070-1076). This model suggests that PDE10A inhibition might alleviate cognitive deficits associated with schizophrenia.

The tissue distribution of PDE10A indicates that PDE10A inhibitors can be used to raise levels of cAMP and/or cGMP within cells that express the PDE10 enzyme, especially neurons that comprise the basal ganglia, and the PDE10A inhibitors of the invention would therefore be useful in treating a variety of associated neuropsychiatric conditions involving the basal ganglia such as neurological and psychiatric disorders, schizophrenia, bipolar disorder, obsessive compulsive disorder, and the like, and may have the benefit of not possessing unwanted side effects, which are associated with the current therapies on the market.

Furthermore, recent publications (WO 2005/120514, WO 2005012485, Cantin et al, Bioorganic & Medicinal Chemistry Letters 17 (2007) 2869-2873) suggest that PDE10A inhibitors may be useful for treatment of obesity and non-insulin dependent diabetes.

With respect to inhibitors of PDE10A, EP 1250923 discloses the use of selective PDE10 inhibitors in general, and papaverine in particular, for the treatment of certain neurologic and psychiatric disorders.

WO 05/113517 discloses benzodiazepine stereospecific compounds as inhibitors of phosphodiesterase, especially types 2 and 4, and the prevention and treatment of pathologies involving a central and/or peripheral disorder. WO 02/88096 discloses benzodiazepine derivatives and their uses as inhibitors of phosphodiesterase, especially type 4 in the therapeutic field. WO 04/41258 discloses benzodiazepinone derivatives and their uses as inhibitors of phosphodiesterase, especially type 2 in the therapeutic field.

Pyrrolodihydroisoquinolines and variants thereof are disclosed as inhibitors of PDE10 in WO 05/03129 and WO 05/02579. Piperidinyl-substituted quinazolines and isoquinolines that serve as PDE10 inhibitors are disclosed in WO 05/82883. WO 06/11040 discloses substituted quinazoline and isoquinoline compounds that serve as inhibitors of PDE10. US 20050182079 discloses substituted tetrahydroisoquinolinyl derivatives of quinazoline and isoquinoline that serve as effective phosphodiesterase (PDE) inhibitors. In particular, US 20050182079 relates to said compounds, which are selective inhibitors of PDE10. Analogously, US 20060019975 discloses piperidine derivatives of quinazoline and isoquinoline that serve as effective phosphodiesterase (PDE) inhibitors. US 20060019975 also relates to compounds that are selective inhibitors of PDE10. WO 06/028957 discloses cinnoline derivatives as inhibitors of phosphodiesterase type 10 for the treatment of psychiatric and neurological syndromes. However, these disclosures do not pertain to the compound of the invention, which are structurally unrelated to any of the known PDE10 inhibitors (Kehler, J. et al. *Expert Opin. Ther. Patents* 2007, 17, 147-158).

The compound of the invention is for the first time disclosed in WO09/152,825 from which application priority is claimed. The compound of the invention proves to be an efficient PDE10A enzyme inhibitor and an in vivo active compound that reverses the PCP induced hyperactivity by 99% and may thus offer alternatives to current marketed treatments for neurodegenerative and/or psychiatric disorders, which are not efficacious in all patients. Hence, there remains a need for alternative methods of treatment.

SUMMARY OF THE INVENTION

The objective of the invention is to provide a compound that is a selective PDE10A enzyme inhibitor.

A further objective of the invention is to provide a compound that has such activity, and has good, preferably improved, solubility, metabolic stability and/or bioavailability compared to prior art compounds.

Another objective of the invention is to provide an effective treatment, in particular long-term treatment, of a human patient, without causing the side effects typically associated with current therapies for neurological and psychiatric disorders.

Further objectives of the invention will become apparent upon reading the specification.

Accordingly, the invention relates to the compound 5,8-Dimethyl-2-[2-(1-methyl-4-phenyl-1H-imidazol-2-yl)-ethyl]-[1,2,4]triazolo[1,5-a]pyrazine of formula I:

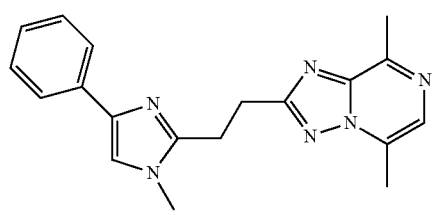

Formula I - compound of the invention

In the context of the present application the term "compound of the invention" includes 5,8-Dimethyl-2-[2-(1-methyl-4-phenyl-1H-imidazol-2-yl)-ethyl]-[1,2,4]triazolo[1,5-a]pyrazine of formula I and ph salts thereof.

The invention further provides the compound of the invention, or a pharmaceutically acceptable acid addition salt thereof, for use as a medicament.

In another aspect, the invention provides a pharmaceutical composition comprising the compound of the invention and a pharmaceutically acceptable carrier, diluent or excipient.

The invention further provides the use of the compound of the invention for the preparation of a medicament for the treatment of a neurodegenerative or psychiatric disorder.

The invention further provides the compound of the invention for use as a medicament.

The invention further provides the compound of the invention for the treatment of a psychiatric disorder selected from the group consisting of schizophrenia, for example of the paranoid, disorganized, catatonic, undifferentiated, or residual type; schizophreniform disorder; schizoaffective disorder, for example of the delusional type or the depressive type; delusional disorder; bipolar disorder, for example bipolar I disorder, bipolar II disorder, and cyclothymic disorder; substance-induced psychotic disorder, for example psychosis induced by alcohol, amphetamine, *cannabis*, cocaine, hallucinogens, inhalants, opioids, or phencyclidine; personality disorder of the paranoid type; and personality disorder of the schizoid type.

Furthermore the invention provides a method of treating a patient suffering from a neurodegenerative disorder, comprising administering to the patient the compound of the invention. In a still further aspect, the invention provides a method of treating a patient suffering from a psychiatric disorder, comprising administering to the patient the compound of the invention. In another embodiment, the invention provides a method of treating a patient suffering from a drug addiction, such as an alcohol, amphetamine, cocaine, or opiate addiction comprising administering to the patient the compound of the invention.

DETAILED DESCRIPTION OF THE INVENTION

Throughout this application the terms PDE 10, PDE 10A and PDE 10A enzyme are used interchangeably.

The compound of the invention has, when tested as described in the section PDE10A enzyme inhibition assay, an $IC_{50}$ value of about 2.2 nM which makes it a useful compound for inhibition of PDE 10A enzyme activity.

Further, the compound has been tested for its ability to reverse phencyclidine (PCP) induced hyperactivity. The reversal of the PCP effect is measured as described in the section "Phencyclidine (PCP) induced hyperactivity". The experiment shows that the compound of the invention is an in vivo active compound that reverses the PCP induced hyperactivity by 99%.

Pharmaceutically Acceptable Salts

The invention also comprises salts of the compound the invention, typically, pharmaceutically acceptable salts. Such salts include pharmaceutically acceptable acid addition salts. Acid addition salts include salts of inorganic acids as well as organic acids.

Representative examples of suitable inorganic acids include hydrochloric, hydrobromic, hydroiodic, phosphoric, sulfuric, sulfamic, nitric acids and the like. Representative examples of suitable organic acids include formic, acetic, trichloroacetic, trifluoroacetic, propionic, benzoic, cinnamic, citric, fumaric, glycolic, itaconic, lactic, methanesulfonic, maleic, malic, malonic, mandelic, oxalic, picric, pyruvic, salicylic, succinic, methane sulfonic, ethanesulfonic, tartaric, ascorbic, pamoic, bismethylene salicylic, ethanedisulfonic, gluconic, citraconic, aspartic, stearic, palmitic, EDTA, glycolic, p-aminobenzoic, glutamic, benzenesulfonic, p-toluenesulfonic acids, theophylline acetic acids, as well as the 8-halotheophyllines, for example 8-bromotheophylline and the like. Further examples of pharmaceutically acceptable inorganic or organic acid addition salts include the pharmaceutically acceptable salts listed in Berge, S. M. et al., *J. Pharm. Sci.* 1977, 66, 2, the contents of which are hereby incorporated by reference.

Furthermore, the compound of this invention may exist in unsolvated as well as in solvated forms with pharmaceutically acceptable solvents such as water, ethanol and the like. In general, the solvated forms are considered equivalent to the unsolvated forms for the purposes of this invention.

Pharmaceutical Compositions

The invention further provides a pharmaceutical composition comprising the compound of the invention and a pharmaceutically acceptable carrier or diluent. The invention also provides a pharmaceutical composition comprising the compound of the invention and a pharmaceutically acceptable carrier or diluent.

The compound of the invention may be administered alone or in combination with pharmaceutically acceptable carriers, diluents or excipients, in either single or multiple doses. The pharmaceutical compositions according to the invention may be formulated with pharmaceutically acceptable carriers or diluents as well as any other known adjuvants and excipients in accordance with conventional techniques such as those disclosed in Remington: The Science and Practice of Pharmacy, 19$^{th}$ Edition, Gennaro, Ed., Mack Publishing Co., Easton, Pa., 1995.

The pharmaceutical compositions may be specifically formulated for administration by any suitable route such as oral, rectal, nasal, pulmonary, topical (including buccal and sublingual), transdermal, intracisternal, intraperitoneal, vaginal and parenteral (including subcutaneous, intramuscular, intrathecal, intravenous and intradermal) routes. It will be appreciated that the route will depend on the general condition and age of the patient to be treated, the nature of the condition to be treated and the active ingredient.

Pharmaceutical compositions for oral administration include solid dosage forms such as capsules, tablets, dragees, pills, lozenges, powders and granules. Where appropriate, the compositions may be prepared with coatings such as enteric coatings or they may be formulated so as to provide controlled release of the active ingredient such as sustained or prolonged release according to methods well known in the art. Liquid dosage forms for oral administration include solutions, emulsions, suspensions, syrups and elixirs.

Pharmaceutical compositions for parenteral administration include sterile aqueous and nonaqueous injectable solutions, dispersions, suspensions or emulsions as well as sterile powders to be reconstituted in sterile injectable solutions or dispersions prior to use. Other suitable administration forms include, but are not limited to, suppositories, sprays, ointments, creams, gels, inhalants, dermal patches and implants.

Typical oral dosages of the compound of the invention range from about 0.001 to about 100 mg/kg body weight per day. Typical oral dosages also range from about 0.01 to about 50 mg/kg body weight per day. Typical oral dosages of the compound of the invention further range from about 0.05 to about 10 mg/kg body weight per day. Oral dosages are usually administered in one or more dosages, typically, one to three dosages per day. The exact dosage will depend upon the frequency and mode of administration, the sex, age, weight and general condition of the patient treated, the nature and severity of the condition treated and any concomitant diseases to be treated and other factors evident to those skilled in the art.

The compositions may also be presented in a unit dosage form by methods known to those skilled in the art. For illustrative purposes, a typical unit dosage form for oral administration may contain from about 0.01 to about 1000 mg, from about 0.05 to about 500 mg, or from about 0.5 mg to about 200 mg of the compound of the invention.

For parenteral routes such as intravenous, intrathecal, intramuscular and similar administration, typical doses are in the order of half the dose employed for oral administration.

The invention also provides a process for making a pharmaceutical composition comprising admixing the compound of the invention and at least one pharmaceutically acceptable carrier or diluent.

The compound of this invention is generally utilized as the free substance or as a pharmaceutically acceptable salt thereof.

For parenteral administration, solutions of the compound of the invention in sterile aqueous solution, aqueous propylene glycol, aqueous vitamin E or sesame or peanut oil may be employed. Such aqueous solutions should be suitably buffered if necessary and the liquid diluent first rendered isotonic with sufficient saline or glucose. The aqueous solutions are particularly suitable for intravenous, intramuscular, subcutaneous and intraperitoneal administration. The compound of the invention may be readily incorporated into known sterile aqueous media using standard techniques known to those skilled in the art.

Suitable pharmaceutical carriers include inert solid diluents or fillers, sterile aqueous solutions and various organic solvents. Examples of solid carriers include lactose, terra alba, sucrose, cyclodextrin, talc, gelatin, agar, pectin, acacia, magnesium stearate, stearic acid and lower alkyl ethers of cellulose. Examples of liquid carriers include, but are not limited to, syrup, peanut oil, olive oil, phospholipids, fatty acids, fatty acid amines, polyoxyethylene and water. Similarly, the carrier or diluent may include any sustained release material known in the art, such as glyceryl monostearate or glyceryl distearate, alone or mixed with a wax. The pharmaceutical compositions formed by combining the compound of the invention and a pharmaceutically acceptable carrier are then readily administered in a variety of dosage forms suitable for the disclosed routes of administration. The compositions may conveniently be presented in unit dosage form by methods known in the art of pharmacy.

Compositions of the invention suitable for oral administration may be presented as discrete units such as capsules or tablets, each containing a predetermined amount of the active ingredient, and optionally a suitable excipient. Furthermore, the orally available compositions may be in the form of a powder or granules, a solution or suspension in an aqueous or non-aqueous liquid, or an oil-in-water or water-in-oil liquid emulsion.

If a solid carrier is used for oral administration, the preparation may be tableted, placed in a hard gelatin capsule in powder or pellet form or it may be in the form of a troche or lozenge. The amount of solid carrier will vary widely but will range from about 25 mg to about 1 g per dosage unit. If a liquid carrier is used, the preparation may be in the form of a syrup, emulsion, soft gelatin capsule or sterile injectable liquid such as an aqueous or non-aqueous liquid suspension or solution.

The pharmaceutical compositions of the invention may be prepared by conventional methods in the art. For example, tablets may be prepared by mixing the active ingredient with ordinary adjuvants and/or diluents and subsequently compressing the mixture in a conventional tabletting machine prepare tablets. Examples of adjuvants or diluents comprise: corn starch, potato starch, talcum, magnesium stearate, gelatin, lactose, gums, and the like. Any other adjuvants or additives usually used for such purposes such as colorings, flavorings, preservatives etc. may be used provided that they are compatible with the active ingredients.

Treatment of Disorders

As mentioned above, the compound of the invention is a PDE10A enzyme inhibitor and as such useful to treat associated neurological and psychiatric disorders.

The invention thus provides a compound of formula I, the compound of the invention as well as a pharmaceutical composition containing such a compound, for use in the treatment of a neurodegenerative disorder, psychiatric disorder or drug addiction in patients; wherein the neurodegenerative disorder is selected from the group consisting of Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline; and wherein the psychiatric disorder is selected from the group consisting of schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; and wherein the drug addiction is an alcohol, amphetamine, cocaine, or opiate addiction.

The compound of the invention may be used in combination with one or more other drugs in the treatment of diseases or conditions for which the compound of the invention have utility, where the combination of the drugs together is safer or more effective than either drug alone. Additionally, the compound of the invention may be used in combination with one or more other drugs that treat, prevent, control, ameliorate, or reduce the risk of side effects or toxicity of the compound of the invention. Such other drugs may be administered, by a route and in an amount commonly used therefore, contemporaneously or sequentially with the compound of the invention. Accordingly, the pharmaceutical compositions of the invention include those that contain one or more other active ingredients, in addition to the compound of the invention. The combinations may be administered as part of a unit dosage form combination product, or as a kit or treatment protocol wherein one or more additional drugs are administered in separate dosage forms as part of a treatment regimen.

The invention provides a method of treating a patient suffering from a neurodegenerative disorder selected from a cognition disorder or movement disorder, which method comprises administering to the patient the compound of the invention.

This invention also provides a method of treating a patient suffering from a psychiatric disorder, which method comprises administering to the patient the compound of the invention. Examples of psychiatric disorders that can be treated according to the invention include, but are not limited to, schizophrenia, for example of the paranoid, disorganized, catatonic, undifferentiated, or residual type; schizophreniform disorder; schizoaffective disorder, for example of the delusional type or the depressive type; delusional disorder; substance-induced psychotic disorder, for example psychosis induced by alcohol, amphetamine, cannabis, cocaine, hallucinogens, inhalants, opioids, or phencyclidine; personality disorder of the paranoid type; and personality disorder of the schizoid type; anxiety disorder is selected from panic disorder; agoraphobia; a specific phobia; social phobia; obsessive-compulsive disorder; post-traumatic stress disorder; acute stress disorder; and generalized anxiety disorder.

The compound of the invention may be administered in combination with at least one neuroleptic agent (which may be a typical or an atypical antipsychotic agent) to provide improved treatment of psychiatric disorders such as schizophrenia. The combinations, uses and methods of treatment of the invention may also provide advantages in treatment of patients who fail to respond adequately or who are resistant to other known treatments.

The invention thus provides a method of treating a patient suffering from a psychiatric disorder, such as schizophrenia, which method comprises administering to the patient the compound of the invention, either alone or as combination therapy together with at least one neuroleptic agent.

The term "neuroleptic agent" as used herein refers to drugs, which have the effect on cognition and behaviour of antipsychotic agent drugs that reduce confusion, delusions, hallucinations, and psychomotor agitation in patients with psychoses. Also known as major tranquilizers and antipsychotic drugs, neuroleptic agents include, but are not limited to: typical antipsychotic drugs, including phenothiazines, further divided into the aliphatics, piperidines, and piperazines, thioxanthenes (e.g., cisordinol), butyrophenones (e.g., haloperidol), dibenzoxazepines (e.g., loxapine), dihydroindolones (e.g., molindone), diphenylbutylpiperidines (e.g., pimozide), and atypical antipsychotic drugs, including benzisoxazoles (e.g., risperidone), sertindole, olanzapine, quetiapine, osanetant and ziprasidone.

Particularly preferred neuroleptic agents for use in the invention are sertindole, olanzapine, risperidone, quetiapine, aripiprazole, haloperidol, clozapine, ziprasidone and osanetant.

The invention further provides a method of treating a patient suffering from a cognition disorder, which method comprises administering to the patient the compound of the invention. Examples of cognition disorders that can be treated according to the invention include, but are not limited to, Alzheimer's disease, multi-infarct dementia, alcoholic dementia or other drug-related dementia, dementia associated with intracranial tumors or cerebral trauma, dementia associated with Huntington's disease or Parkinson's disease, or AIDS-related dementia; delirium; amnestic disorder; post-traumatic stress disorder; mental retardation; a learning disorder, for example reading disorder, mathematics disorder, or a disorder of written expression; attention-deficit/hyperactivity disorder; and age-related cognitive decline.

This invention also provides a method of treating a movement disorder in a patient, which method comprises administering to the patient the compound of the invention. Examples of movement disorders that can be treated according to the invention include, but are not limited to, Huntington's disease and dyskinesia associated with dopamine agonist therapy. This invention further provides a method of treating a movement disorder selected from Parkinson's disease and restless leg syndrome, which comprises administering to the patient the compound of the invention.

This invention also provides a method of treating a mood disorder, which method comprises administering to the patient the compound of the invention. Examples of mood disorders and mood episodes that can be treated according to the invention include, but are not limited to, major depressive episode of the mild, moderate or severe type, a manic or mixed mood episode, a hypomanic mood episode; a depressive episode with a typical features; a depressive episode with melancholic features; a depressive episode with catatonic features; a mood episode with postpartum onset; post-stroke depression; major depressive disorder; dysthymic disorder; minor depressive disorder; premenstrual dysphoric disorder; post-psychotic depressive disorder of schizophrenia; a major depressive disorder superimposed on a psychotic disorder such as delusional disorder or schizophrenia; a bipolar disorder, for example bipolar I disorder, bipolar II disorder, and cyclothymic disorder. It is understood that a mood disorder is a psychiatric disorder.

This invention further provides a method of treating a drug addiction, for example an alcohol, amphetamine, cocaine, or opiate addiction, in a patient which method comprises administering to said patient an amount of the compound of the invention effective in treating drug addiction.

The term "drug addiction", as used herein, means an abnormal desire for a drug and is generally characterized by motivational disturbances such a compulsion to take the desired drug and episodes of intense drug craving.

Drug addiction is widely considered a pathological state. The disorder of addiction involves the progression of acute drug use to the development of drug-seeking behavior, the vulnerability to relapse, and the decreased, slowed ability to respond to naturally rewarding stimuli. For example, The Diagnostic and Statistical Manual of Mental Disorders, Fourth Edition (DSM-IV) has categorized three stages of addiction: preoccupation/anticipation, binge/intoxication, and withdrawal/negative affect. These stages are characterized, respectively, everywhere by constant cravings and preoccupation with obtaining the substance; using more of the substance than necessary to experience the intoxicating effects; and experiencing tolerance, withdrawal symptoms, and decreased motivation for normal life activities.

This invention further provides a method of treating a disorder comprising as a symptom a deficiency in attention and/or cognition in a patient which method comprises administering to said patient an amount of the compound of the invention effective in treating said disorder.

Other disorders that can be treated according to the invention are obsessive/compulsive disorders, Tourette's syndrome and other tic disorders.

As used herein, and unless otherwise indicated, a "neurodegenerative disorder or condition" refers to a disorder or condition that is caused by the dysfunction and/or death of neurons in the central nervous system. The treatment of these disorders and conditions can be facilitated by administration of an agent which prevents the dysfunction or death of neurons at risk in these disorders or conditions and/or enhances the function of damaged or healthy neurons in such a way as to compensate for the loss of function caused by the dysfunction or death of at-risk neurons. The term "neurotrophic agent" as used herein refers to a substance or agent that has some or all of these properties.

Examples of neurodegenerative disorders and conditions that can be treated according to the invention include, but are not limited to, Parkinson's disease; Huntington's disease; dementia, for example Alzheimer's disease, multi-infarct dementia, AIDS-related dementia, and Fronto temperal Dementia; neurodegeneration associated with cerebral trauma; neurodegeneration associated with stroke, neurodegeneration associated with cerebral infarct; hypoglycemia-induced neurodegeneration; neurodegeneration associated with epileptic seizure; neurodegeneration associated with neurotoxin poisoning; and multi-system atrophy.

In one embodiment of the invention, the neurodegenerative disorder or condition involves neurodegeneration of striatal medium spiny neurons in a patient.

In a further embodiment of the invention, the neurodegenerative disorder or condition is Huntington's disease.

In another embodiment, the invention provides a method of treating a patient to reduce body fat or body weight, or to treat non-insulin demanding diabetes mellitus (NIDDM), metabolic syndrome, or glucose intolerance, comprising administering to the patient in need thereof the compound of the invention. In some embodiments, the patient is overweight or obese and the compound of the invention is administered orally. In another preferred embodiment, the method further comprising administering a second therapeutic agent to the patient, preferably an anti-obesity agent, e.g., rimonabant, orlistat, sibutramine, bromocriptine, ephedrine, leptin, pseudoephedrine, or peptide YY3-36, or analogs thereof.

rated by reference and were set forth in its entirety (to the maximum extent permitted by law).

Headings and sub-headings are used herein for convenience only, and should not be construed as limiting the invention in any way.

The use of any and all examples, or exemplary language (including "for instance", "for example", "e.g.", and "as such") in the present specification is intended merely to better illuminate the invention, and does not pose a limitation on the scope of invention unless otherwise indicated.

The citation and incorporation of patent documents herein is done for convenience only, and does not reflect any view of the validity, patentability and/or enforceability of such patent documents.

The invention includes all modifications and equivalents of the patient-matter recited in the claims appended hereto, as permitted by applicable law.

EXPERIMENTAL SECTION

Preparation of the Compound of the Invention

Compound of the invention may be prepared as described in the following reaction scheme 1

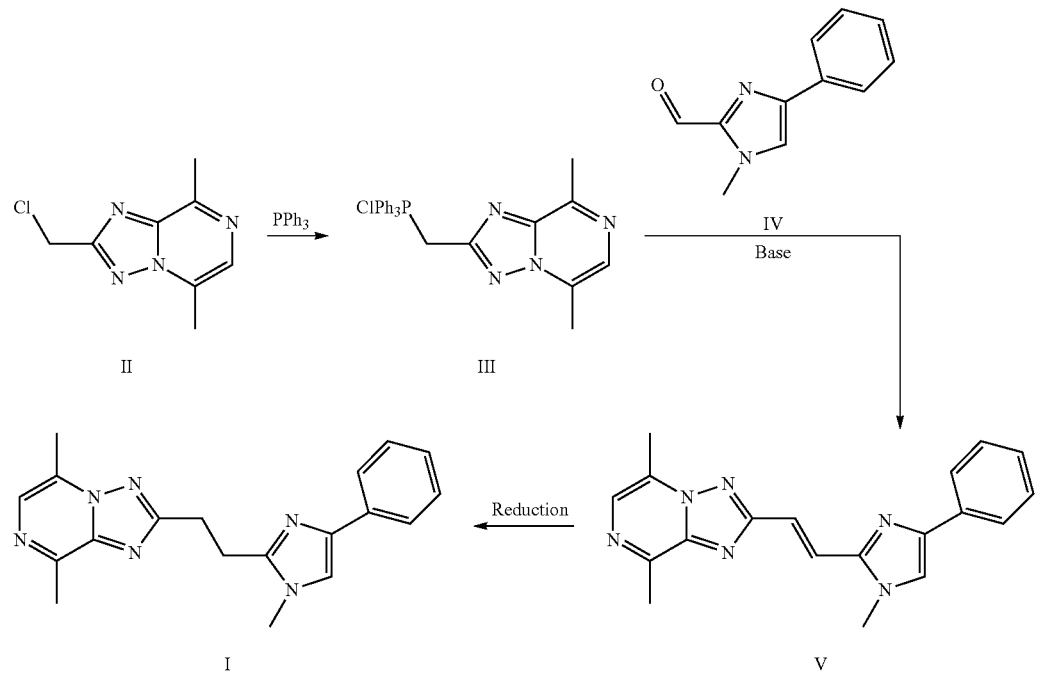

The term "metabolic syndrome" as used herein refers to a constellation of conditions that place people at high risk for coronary artery disease. These conditions include type 2 diabetes, obesity, high blood pressure, and a poor lipid profile with elevated LDL ("bad") cholesterol, low HDL ("good") cholesterol, and elevated triglycerides. All of these conditions are associated with high blood insulin levels. The fundamental defect in the metabolic syndrome is insulin resistance in both adipose tissue and muscle.

All references, including publications, patent applications and patents, cited herein are hereby incorporated by reference in their entirety and to the same extent as if each reference were individually and specifically indicated to be incorpo- Specifically, compounds of the present invention can be prepared by reduction of an alkene of formula V by hydrogenation using a transition metal catalyst, such as palladium metal, together with a hydrogen source, such as hydrogen gas, ammonium hydrogen carbonate, or cyclohexadiene. Said alkenes of formula V can be prepared by the Wittig reaction between a phosphonium salt of formula III and an aldehyde of formula IV in a suitable solvent, such as tetrahydrofuran, in the presence of a suitable base, such as 1,8-diazabicyclo [5.4.0]undec-7-ene. Phosphonium salt of formula III are readily available by reaction of compounds of formula II with triphenylphosphine by methods known to chemists skilled in the art. Aldehydes of formula IV are readily available and known in the art as described in e.g. Journal of Medicinal Chemistry (2009), 52(21), 6535-6538, or WO-2004024705 and U.S. Pat. No. 4,826,833.

The electrophile II (scheme 2) can be prepared from the dimethylchloropyrazine of formula VI known in the art as described in e.g. Journal of the Chemical Society, Perkin Transactions 1: Organic and Bio-Organic Chemistry 1996, (19), 2345-2350 and Journal of Heterocyclic Chemistry (1981), 18(3), 555-8. The compound VI can be converted to the aminopyrazine of formula VII as described in the literature e.g. Science of Synthesis (2004), 16 751-844 and Synthesis 1994, (9), 931-4. The amination of six-membered heterocycles like pyrazines of formula VIII using an electrophilic amination reagent like e.g. O-Mesitylenesulfonylhydroxylamine is well known in the art as described in e.g. Organic Process Research & Development 2009, 13, 263-267. The reaction of compound of formula VIII with methyl chloroacetate gives the electrophile II.

Preparative LC-MS-purification was performed on a PE Sciex API 150EX instrument with atmospheric pressure chemical ionization. Column: 50×20 mm YMC ODS-A with 5 μm particle size; Method: Linear gradient elution with A:B=80:20 to 0:100 in 7 minutes and with a flow rate of 22.7 mL/minute. Fraction collection was performed by split-flow MS detection.

$^1$H NMR spectra were recorded at 500.13 MHz on a Bruker Avance AV500 instrument or at 250.13 MHz on a Bruker Avance DPX250 instrument. TMS was used as internal reference standard. Chemical shift values are expressed in ppm. The following abbreviations are used for multiplicity of NMR signals: s=singlet, d=doublet, t=triplet, q=quartet, qui=quintet, h=heptet, dd=double doublet, dt=double triplet, dq=double quartet, tt=triplet of triplets, m=multiplet, br s=broad singlet and br=broad signal.

Abbreviations are in accordance with to the ACS Style Guide: "The ACS Styleguide—A manual for authors and editors" Janet S. Dodd, Ed. 1997, ISBN: 0841234620

Preparation of Intermediates

2-Chloromethyl-5,7-dimethyl-[1,2,4]triazolo[1,5-a]pyrimidine

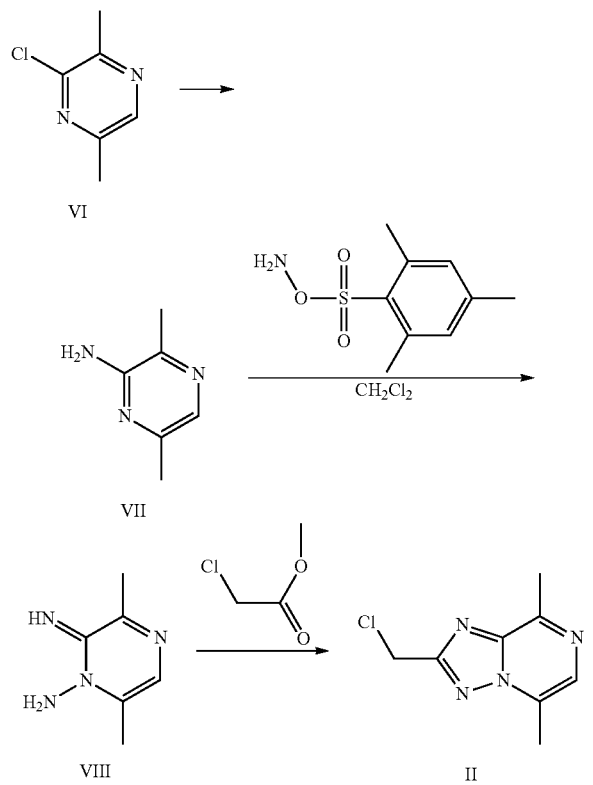

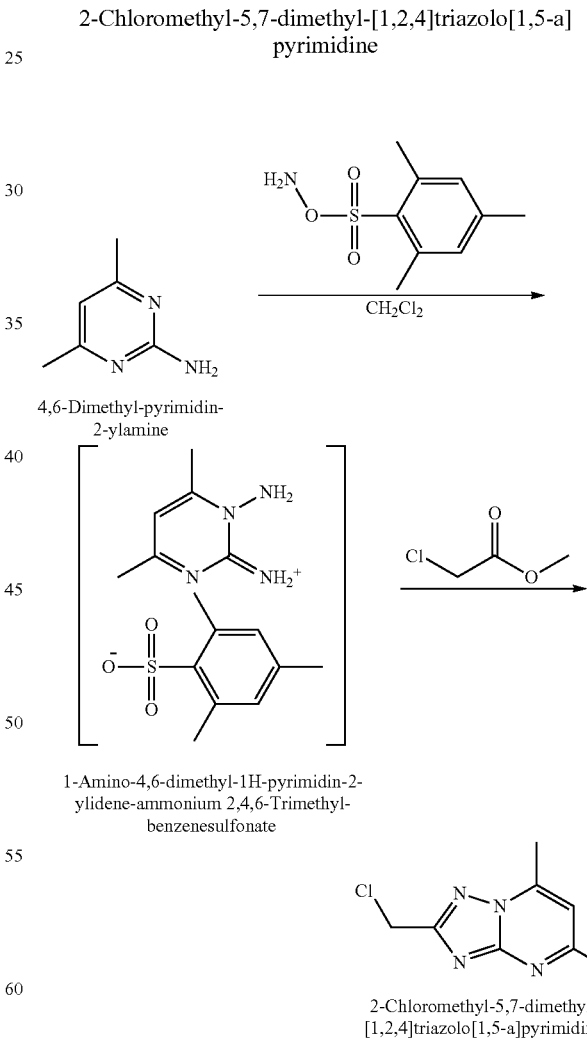

The invention disclosed herein is further illustrated by the following non-limiting examples.
General Methods
Analytical LC-MS data were obtained using one of the following method:
Method A:
A PE Sciex API 150EX instrument equipped with atmospheric pressure photo ionisation and a Shimadzu LC-8A/SLC-10A LC system was used. Column: 4.6×30 mm Waters Symmetry C18 column with 3.5 μm particle size; Column temperature: 60° C.; Solvent system: A=water/trifluoroacetic acid (100:0.05) and B=water/acetonitrile/trifluoroacetic acid (5:95:0.035); Method: Linear gradient elution with A:B=90:10 to 0:100 in 2.4 minutes and with a flow rate of 3.3 mL/min.

To a solution of 4,6-Dimethyl-pyrimidin-2-ylamine (25 g, 200 mmol) in 400 mL of CH$_2$Cl$_2$ was added dropwise a solution of hydroxylamine-2,4,6-Trimethyl-benzenesulfonate (105 g, 488 mmol) in 300 mL of CH$_2$Cl$_2$ at 0° C., and the mixture was stirred at 0° C. for 1 h and filtered. The solid collected was washed with $CH_2Cl_2$ (100 mL) to give 1-Amino-4,6-dimethyl-1H-pyrimidin-2-ylidene-ammonium 2,4,6-Trimethyl-benzenesulfonate (40 g, yield: 62%).

A mixture of 1-Amino-4,6-dimethyl-1H-pyrimidin-2-ylidene-ammonium 2,4,6-Trimethyl-benzenesulfonate (40 g, 0.1 mol) and NaOH (10 g, 0.2 mol) in 500 mL of EtOH was stirred at 50-60° C. for 1 hour. After chloroacetic acid methyl ester (16.6 g, 0.15 mol) was added, the resultant mixture was stirred at reflux for 4 hours. After being concentrated under reduce pressure, the residue was diluted with water (1000 mL) and extracted with $CH_2Cl_2$ (300 mL×3). The combined organic layers were washed with brine (200 mL), dried over $Na_2SO_4$, filtered, and concentrated under vacuum. The residue was purified by column chromatography on silica gel (petroleum ether/EtOAc=2/1) to give 2 g of 2-Chloromethyl-5,7-dimethyl-[1,2,4]triazolo[1,5-a]pyrimidine in 9% yield. $^1H$ NMR (300 MHz, DMSO-$d_6$): δ8.55 (s, 1H), 6.25 (s, 2H), 4.05 (s, 3H), 3.95 (s, 3H); LC-MS (MH$^+$): m/z=196.9, $t_R$ (min, method A)=0.52

The following intermediate was prepared analogously: 2-Chloromethyl-5,8-dimethyl-[1,2,4]-triazolo[1,5-a]pyrazine from 2-amino-3,6-dimethylpyrazine. 60% yield, $^1H$ NMR (500 MHz, CDCl$_3$): δ7.91 (s, 1H), 4.87 (s, 2H), 2.91 (s, 3H), 2.74 (s, 3H), LC-MS: m/z=196.9 (MH$^+$), $t_R$=0.64 min, method A trans-5,8-Dimethyl-2-[(E)-2-(1-methyl-4-phenyl-1H-imidazol-2-yl)-vinyl]-[1,2,4]triazolo[1,5-a]pyrazine

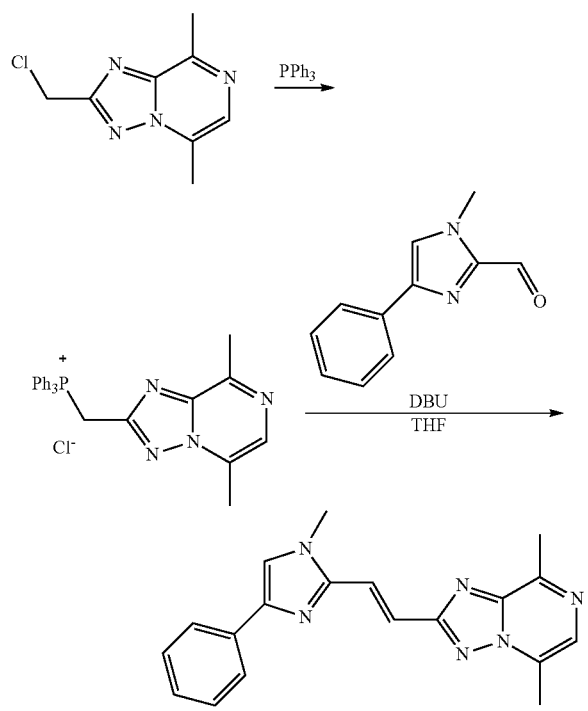

A solution of 2-chloromethyl-5,8-dimethyl-[1,2,4]-triazolo[1,5-a]pyrazine (1.351 g, 6.87 mmol) and triphenylphosphine (1.80 g, 6.87 mmol) in acetonitrile 150 mL was heated at reflux for 12 h. The solvents were removed in vacuo and the residue slurried in ether, filtered and dried to yield (5,8-Dimethyl-[1,2,4]triazolo[1,5-a]pyrazin-2-ylmethyl)-triphenyl-phosphonium; chloride as an off white solid (2.412 g, 74.9%). LC-MS: m/z=423.2 ([M-Cl]$^+$), tR=0.86 min, method A.

A solution of 1-methyl-4-phenyl-1H-imidazole-2-carbaldehyde (220 mg, 1.18 mmol) in dry THF was added to (5,8-Dimethyl-[1,2,4]triazolo[1,5-a]pyrazin-2-ylmethyl)-triphenyl-phosphonium; chloride (500 mg, 1.18 mmol) under argon and 1,8-diazabicyclo[5.4.0]undec-7-ene (176 μL, 1.18 mmol) was added. The reaction mixture was stirred at room temperature for 2 h after which it was evaporated onto silica gel (2 g). Silica gel chromatography (gradient elution; A:B 50:50→100:0, where A is ethyl acetate and B is heptane) afforded the title compound (334 mg, 79%) as an off white solid. LC-MS: m/z=331.4 (MH$^+$), $t_R$=0.65 min, method A.

Preparation of the Compound of the Invention

Example 1

5,8-Dimethyl-2-[2-(1-methyl-4-phenyl-1H-imidazol-2-yl)-ethyl]-[1,2,4]triazolo[1,5-a]pyrazine

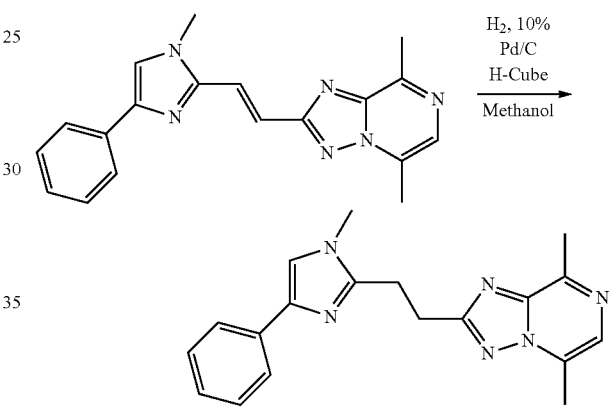

A solution of trans-5,8-dimethyl-2-[(E)-2-(1-methyl-4-phenyl-1H-imidazol-2-yl)-vinyl]-imidazo[1,2-a]pyrazine (330 mg, 1.0 mmol) in methanol (50 mL) was passed through a H-Cube® Continuous-flow Hydrogenation Reactor (ThalesNano) at a flow rate of 1 mL/min through a small cartridge of 10% Pd/C (THS01111) with an internal temperature of 25° C. and 1 bar of hydrogen pressure. Evaporation of the volatiles afforded the title compound (178 mg, 51%). LC-MS: m/z=333.2 (MH$^+$), $t_R$=0.57 min, method A.

Pharmacological Testing

PDE10A Enzyme

Active PDE10A enzyme is prepared in a number of ways for use in PDE assays (Loughney, K. et al. *Gene* 1999, 234, 109-117; Fujishige, K. et al. *Eur J Biochem*. 1999, 266, 1118-1127 and Soderling, S. et al. *Proc. Natl. Acad. Sci.* 1999, 96, 7071-7076). PDE10A can be expressed as full-length proteins or as truncated proteins, as long as they express the catalytic domain. PDE10A can be prepared in different cell types, for example insect cells or *E. coli*. An example of a method to obtain catalytically active PDE10A is as follows: The catalytic domain of human PDE10A (amino acids 440-779 from the sequence with accession number NP 006652) is amplified from total human brain total RNA by standard RT-PCR and is cloned into the BamH1 and Xho1 sites of the pET28a vector (Novagen). Expression in coli is performed according to standard protocols. Briefly, the expression plasmids are transformed into the BL21(DE3) *E. coli* strain, and 50 mL cultures inoculated with the cells allowed to grow to an OD600 of 0.4-0.6 before protein expression is induced with 0.5 mM IPTG. Following induction, the cells are incubated overnight at room temperature, after which the cells are collected by centrifugation. Cells expressing PDE10A are resuspended in 12 mL (50 mM TRIS-HCl-pH 8.0, 1 mM $MgCl_2$ and protease inhibitors). The cells are lysed by sonication, and after all cells are lysed, TritonX100 is added according to Novagen protocols. PDE10A is partially purified on Q sepharose and the most active fractions were pooled.

PDE10A Inhibition Assay

A PDE10A assay may for example, be performed as follows: The assay is performed in 60 uL samples containing a fixed amount of the relevant PDE enzyme (sufficient to convert 20-25% of the cyclic nucleotide substrate), a buffer (50 mM HEPES 7.6; 10 mM $MgCl_2$; 0.02% Tween20), 0.1 mg/ml BSA, 225 pCi of $^3$H-labelled cyclic nucleotide substrate, tritium labeled cAMP to a final concentration of 5 nM and varying amounts of inhibitors. Reactions are initiated by addition of the cyclic nucleotide substrate, and reactions are allowed to proceed for one hr at room temperature before being terminated through mixing with 15 uL 8 mg/mL yttrium silicate SPA beads (Amersham). The beads are allowed to settle for one hr in the dark before the plates are counted in a Wallac 1450 Microbeta counter. The measured signal can be converted to activity relative to an uninhibited control (100%) and $IC_{50}$ values can be calculated using the Xlfit extension to EXCEL.

In the context of the invention the assay was performed in 60 uL assay buffer (50 mM HEPES pH 7.6; 10 mM $MgCl_2$; 0.02% Tween20) containing enough PDE10A to convert 20-25% of 10 nM $^3$H-cAMP and varying amounts of inhibitors. Following a 1 hour incubation the reactions were terminated by addition of 15 uL 8 mg/mL yttrium silicate SPA beads (Amersham). The beads were allowed to settle for one hr in the dark before the plates were counted in a Wallac 1450 Microbeta counter. $IC_{50}$ values were calculated by non linear regression using XLfit (IDBS).

Results of the experiments showed that the tested compound of the invention inhibit the PDE10A enzyme with $IC_{50}$ value around 2.2 nM.

Phencyclidine (PCP) Induced Hyperactivity

Male mice (NMRI, Charles River) weighing 20-25 g were used. Eight mice were used in each group receiving the test compound (5 mg/kg) plus PCP (2.3 mg/kg) including the parallel control groups receiving the vehicle of the test compound plus PCP or vehicle injections only. The injection volume was 10 ml/kg. The experiment was made in normal light conditions in an undisturbed room. The test substance was injected per oss 60 min before injection of PCP, which is administered subcutaneous.

Immediately after injection of PCP the mice were placed individually in special designed test cage (20 cm×32 cm). The activity was measured by 5×8 infrared light sources and photocells spaced by 4 cm. The light beams cross the cage 1.8 cm above the bottom of the cage. Recording of a motility count requires interruption of adjacent light beams, thus avoiding counts induced by stationary movements of the mice.

Motility was recorded in 5 min intervals for a period of 1 hour. The drug effect was calculated on the total counts during the 1 hour behavioral test period in the following manner:

The mean motility induced by vehicle treatment in the absence of PCP was used as baseline. The 100 percent effect of PCP was accordingly calculated to be total motility counts minus baseline. The response in groups receiving test compound was thus determined by the total motility counts minus baseline, expressed in percent of the similar result recorded in the parallel PCP control group. The percent responses were converted to percent reversal of the PCP induced hyperactivity.

Results of the experiments showed that the compound of the invention is an in vivo active compound that reverses the PCP induced hyperactivity by 99%.

What is claimed is:

1. A method of treating a psychiatric disorder in a patient comprising administering a therapeutically effective amount of 5,8-dimethyl-2-[2-(1-methyl-4-phenyl-1H-imidazol-2-yl)-ethyl]-[1,2,4]triazolo[1,5-a]pyrazine to the patient, wherein the psychiatric disorder is schizophrenia, schizophreniform disorder or schizoaffective disorder.

2. The method of claim 1, wherein the psychiatric disorder is schizophrenia.

3. The method of claim 2, wherein the psychiatric disorder is schizophrenia of the paranoid, disorganized, catatonic, undifferentiated, or residual type.

4. The method of claim 1, wherein the psychiatric disorder is schizophreniform disorder.

5. The method of claim 1, wherein the psychiatric disorder is schizoaffective disorder.

6. The method of claim 5, wherein the schizoaffective disorder is of the delusional type or the depressive type.

7. The method of claim 2 wherein the 5,8-dimethyl-2-[2-(1-methyl-4-phenyl-1H-imidazol-2-yl)-ethyl]-[1,2,4]triazolo[1,5-a]pyrazine is administered in combination with one or more neuroleptic agents.

8. The method of claim 7, wherein the neuroleptic agent is sertindole, olanzapine, risperidone, quetiapine, aripiprazole, haloperidol, clozapine, ziprasidone or osanetant.

9. The method of claim 4 wherein the 5,8-dimethyl-2-[2-(1-methyl-4-phenyl-1H-imidazol-2-yl)-ethyl]-[1,2,4]triazolo[1,5-a]pyrazine is administered in combination with one or more neuroleptic agents.

10. The method of claim 9, wherein the neuroleptic agent is sertindole, olanzapine, risperidone, quetiapine, aripiprazole, haloperidol, clozapine, ziprasidone or osanetant.

11. The method of claim 5 wherein the 5,8-dimethyl-2-[2-(1-methyl-4-phenyl-1H-imidazol-2-yl)-ethyl]-[1,2,4]triazolo[1,5-a]pyrazine is administered in combination with one or more neuroleptic agents.

12. The method of claim 11 wherein the neuroleptic agent is sertindole, olanzapine, risperidone, quetiapine, aripiprazole, haloperidol, clozapine, ziprasidone or osanetant.

* * * * *